United States Patent
Mosnier et al.

(10) Patent No.: US 11,769,251 B2
(45) Date of Patent: Sep. 26, 2023

(54) SYSTEMS AND METHODS FOR MEDICAL IMAGE ANALYSIS

(71) Applicant: Medicrea International, Rillieux-la-Pape (FR)

(72) Inventors: Thomas Mosnier, Rochetaillee sur Saone (FR); Denys Sournac, Reyrieux (FR)

(73) Assignee: MEDICREA INTERNATIONAL

( * ) Notice: Subject to any disclaimer, the term of this patent is extended or adjusted under 35 U.S.C. 154(b) by 386 days.

(21) Appl. No.: 17/130,504

(22) Filed: Dec. 22, 2020

(65) Prior Publication Data

US 2021/0201483 A1    Jul. 1, 2021

Related U.S. Application Data

(60) Provisional application No. 62/953,677, filed on Dec. 26, 2019.

(51) Int. Cl.
  *G06T 7/00*  (2017.01)
  *G06T 7/13*  (2017.01)
  (Continued)

(52) U.S. Cl.
  CPC .............. *G06T 7/0012* (2013.01); *G06T 7/13* (2017.01); *G06T 11/203* (2013.01); *G16H 50/20* (2018.01);
  (Continued)

(58) Field of Classification Search
  CPC ........ G06T 7/0012; G06T 7/13; G06T 11/203
  See application file for complete search history.

(56) References Cited

U.S. PATENT DOCUMENTS

| 4,382,438 A | 5/1983 | Jacobs |
| 5,006,984 A | 4/1991 | Steele |

(Continued)

FOREIGN PATENT DOCUMENTS

| AU | 2015258176 A1 | 12/2015 |
| AU | 2015202416 B2 | 3/2017 |

(Continued)

OTHER PUBLICATIONS

Roberts, M. G., Oh, T., Pacheco, E. M. B., Mohankumar, R., Cootes, T. F., & Adams, J. E. (2011). Semi-automatic determination of detailed vertebral shape from lumbar radiographs using active appearance models. In Osteoporosis International (vol. 23, Issue 2, pp. 655-664). Springer Science and Business (Year: 2011).*

(Continued)

*Primary Examiner* — John Villecco
*Assistant Examiner* — Courtney Joan Nelson
(74) *Attorney, Agent, or Firm* — FOX ROTHSCHILD LLP (57) ABSTRACT

Systems, instruments, and methods for medical treatment are disclosed. The methods comprise, by a computing device: receiving information identifying at least one first point on a body part shown in a medical image; overlaying a first mark on the medical image for the at least one first point; generating a spline based at least on the first mark; overlaying a second mark for the spline on the medical image; identifying a location of at least one second point on the body part shown in the medical image based on the first and second marks; overlaying a third mark for the at least one second point on the medical image; and using at least the third mark to facilitate the medical treatment of an individual whose body part is shown in the medical image.

18 Claims, 7 Drawing Sheets

(51) Int. Cl.
*G16H 50/20* (2018.01)
*G06T 11/20* (2006.01)
(52) U.S. Cl.
CPC ............... *G06T 2207/30012* (2013.01); *G06T 2210/41* (2013.01)

(56) References Cited

U.S. PATENT DOCUMENTS

| | | | |
|---|---|---|---|
| 5,163,440 A | 11/1992 | DeLuca et al. |
| 5,209,752 A | 5/1993 | Ashman et al. |
| 5,224,035 A | 6/1993 | Yamashita et al. |
| 5,251,127 A | 10/1993 | Raab |
| 5,291,901 A | 3/1994 | Graf |
| 5,305,203 A | 4/1994 | Raab |
| 5,312,405 A | 5/1994 | Korotko et al. |
| 5,413,116 A | 5/1995 | Radke et al. |
| 5,514,180 A | 5/1996 | Heggeness et al. |
| 5,667,506 A | 9/1997 | Sutterlin |
| 5,748,767 A | 5/1998 | Raab |
| 5,785,663 A | 7/1998 | Sarvazyan |
| 6,015,409 A | 1/2000 | Jackson |
| 6,213,958 B1 | 4/2001 | Winder |
| 6,282,437 B1 | 8/2001 | Franck et al. |
| 6,302,888 B1 | 10/2001 | Mellinger et al. |
| 6,364,849 B1 | 4/2002 | Wilcox |
| 6,385,475 B1 | 5/2002 | Cinquin et al. |
| 6,409,684 B1 | 6/2002 | Wilk |
| 6,443,953 B1 | 9/2002 | Perra et al. |
| 6,499,488 B1 | 12/2002 | Hunter et al. |
| 6,565,519 B2 | 5/2003 | Benesh |
| 6,585,666 B2 | 7/2003 | Suh et al. |
| 6,711,432 B1 | 3/2004 | Krause et al. |
| 6,715,213 B2 | 4/2004 | Richter |
| 6,716,213 B2 | 4/2004 | Shitoto |
| 6,746,449 B2 | 6/2004 | Jones et al. |
| 6,786,930 B2 | 9/2004 | Biscup |
| 7,066,938 B2 | 6/2006 | Slivka et al. |
| 7,095,881 B2 * | 8/2006 | Lelong .................... G06T 7/593 382/294 |
| 7,338,526 B2 | 3/2008 | Steinberg |
| 7,509,183 B2 | 3/2009 | Lin et al. |
| 7,534,263 B2 | 5/2009 | Burdulis, Jr. et al. |
| 7,542,791 B2 | 6/2009 | Mire et al. |
| 7,570,791 B2 | 8/2009 | Frank et al. |
| 7,606,613 B2 | 10/2009 | Simon et al. |
| 7,611,522 B2 | 11/2009 | Gorek |
| 7,618,451 B2 | 11/2009 | Berez et al. |
| 7,634,119 B2 | 12/2009 | Tsougarakis et al. |
| 7,635,367 B2 | 12/2009 | Groiso |
| 7,639,866 B2 | 12/2009 | Pomero et al. |
| 7,660,623 B2 | 2/2010 | Hunter et al. |
| 7,674,293 B2 | 3/2010 | Kuiper et al. |
| 7,715,602 B2 | 5/2010 | Richard |
| 7,763,054 B2 | 7/2010 | Clement et al. |
| 7,824,413 B2 | 11/2010 | Varieur et al. |
| 7,835,778 B2 | 11/2010 | Foley et al. |
| 7,840,253 B2 | 11/2010 | Tremblay et al. |
| 7,862,593 B2 | 1/2011 | Clement et al. |
| 7,918,887 B2 | 4/2011 | Roche |
| 7,953,471 B2 | 5/2011 | Clayton et al. |
| 7,974,677 B2 | 7/2011 | Mire et al. |
| 7,981,158 B2 | 7/2011 | Fitz et al. |
| 7,996,061 B2 | 8/2011 | Mollard et al. |
| 7,996,064 B2 | 8/2011 | Simon et al. |
| 8,000,926 B2 | 8/2011 | Roche et al. |
| 8,036,441 B2 | 10/2011 | Frank et al. |
| 8,038,716 B2 | 10/2011 | Duggal et al. |
| 8,046,050 B2 | 10/2011 | Govari et al. |
| 8,066,708 B2 | 11/2011 | Lang et al. |
| 8,077,950 B2 | 12/2011 | Tsougarakis et al. |
| 8,083,778 B2 | 12/2011 | Clement et al. |
| 8,105,330 B2 | 1/2012 | Fitz et al. |
| 8,142,842 B2 | 3/2012 | Sugita et al. |
| 8,196,825 B2 | 6/2012 | Turner et al. |
| 8,211,109 B2 | 7/2012 | Groiso |
| 8,211,153 B2 | 7/2012 | Shaolian et al. |
| 8,234,097 B2 | 7/2012 | Steines et al. |
| 8,241,296 B2 | 8/2012 | Wasielewski |
| 8,246,680 B2 | 8/2012 | Betz et al. |
| 8,265,790 B2 | 9/2012 | Amiot et al. |
| 8,270,253 B1 | 9/2012 | Roche et al. |
| 8,275,594 B2 | 9/2012 | Lin et al. |
| 8,308,772 B2 | 11/2012 | Clement et al. |
| 8,308,775 B2 | 11/2012 | Clement et al. |
| 8,337,501 B2 | 12/2012 | Fitz et al. |
| 8,357,111 B2 | 1/2013 | Caillouette et al. |
| 8,357,166 B2 | 1/2013 | Aram et al. |
| 8,372,075 B2 | 2/2013 | Groiso |
| 8,377,073 B2 | 2/2013 | Wasielewski |
| 8,394,142 B2 | 3/2013 | Bertagnoli et al. |
| 8,398,681 B2 | 3/2013 | Augostino et al. |
| 8,400,312 B2 | 3/2013 | Hotokebuchi et al. |
| 8,414,592 B2 | 4/2013 | Quiro |
| 8,442,621 B2 | 5/2013 | Gorek et al. |
| 8,457,930 B2 | 6/2013 | Schroeder |
| 8,465,527 B2 | 6/2013 | Clement |
| 8,494,805 B2 | 7/2013 | Roche et al. |
| 8,506,632 B2 | 8/2013 | Ganem et al. |
| 8,532,806 B1 | 9/2013 | Masson |
| 8,535,337 B2 | 9/2013 | Chang et al. |
| 8,549,888 B2 | 10/2013 | Isaacs |
| 8,556,983 B2 | 10/2013 | Bojarski et al. |
| 8,588,892 B2 | 11/2013 | Hladio et al. |
| 8,636,776 B2 | 1/2014 | Rosenberg et al. |
| 8,672,948 B2 | 3/2014 | Lemaitre |
| 8,685,093 B2 | 4/2014 | Anderson et al. |
| 8,690,888 B2 | 4/2014 | Stein et al. |
| 8,705,829 B2 | 4/2014 | Frank et al. |
| 8,718,820 B2 | 5/2014 | Amiot et al. |
| 8,758,357 B2 | 6/2014 | Frey |
| 8,775,133 B2 | 7/2014 | Schroeder |
| 8,777,877 B2 | 7/2014 | Stein et al. |
| 8,784,339 B2 | 7/2014 | Stein et al. |
| 8,792,694 B2 * | 7/2014 | Batman ................. G06T 7/0012 382/128 |
| 8,801,786 B2 | 8/2014 | Bernard et al. |
| 8,814,877 B2 | 8/2014 | Wasielewski |
| 8,814,915 B2 | 8/2014 | Hess et al. |
| 8,852,237 B2 | 10/2014 | Kalfas et al. |
| 8,855,389 B1 | 10/2014 | Hoffmann et al. |
| 8,864,764 B2 | 10/2014 | Groiso |
| 8,870,889 B2 | 10/2014 | Frey |
| 8,900,316 B2 | 12/2014 | Lenz et al. |
| 8,911,448 B2 | 12/2014 | Stein |
| 8,926,673 B2 | 1/2015 | Clement et al. |
| 8,945,133 B2 | 2/2015 | Stein et al. |
| 8,956,416 B2 | 2/2015 | McCarthy |
| 8,974,467 B2 | 3/2015 | Stone |
| 8,983,813 B2 | 3/2015 | Miles et al. |
| 8,998,962 B2 | 4/2015 | Birch |
| 9,011,448 B2 | 4/2015 | Roche et al. |
| 9,034,037 B2 | 5/2015 | Fiere et al. |
| 9,039,772 B2 | 5/2015 | Park et al. |
| 9,056,017 B2 | 6/2015 | Kotlus |
| 9,066,701 B1 | 6/2015 | Finley et al. |
| 9,066,734 B2 | 6/2015 | Schoenefeld et al. |
| 9,078,755 B2 | 7/2015 | Mahfouz |
| 9,101,492 B2 | 8/2015 | Mangione et al. |
| 9,115,998 B2 | 8/2015 | Proulx et al. |
| 9,119,572 B2 | 9/2015 | Gorek et al. |
| 9,119,671 B2 | 9/2015 | Kast |
| 9,125,680 B2 | 9/2015 | Kostrzewski et al. |
| 9,144,440 B2 | 9/2015 | Aminian |
| 9,144,470 B2 | 9/2015 | Proulx et al. |
| 9,168,153 B2 | 10/2015 | Bettenga |
| 9,173,661 B2 | 11/2015 | Metzger et al. |
| 9,180,015 B2 | 11/2015 | Fitz et al. |
| 9,192,412 B2 | 11/2015 | Meyrat et al. |
| 9,198,678 B2 | 12/2015 | Frey et al. |
| 9,232,955 B2 | 1/2016 | Bonin, Jr. et al. |
| 9,233,001 B2 | 1/2016 | Miles et al. |
| 9,237,952 B2 | 1/2016 | Kurtz |
| 9,248,023 B2 | 2/2016 | Ries et al. |
| 9,250,620 B2 | 2/2016 | Kotlus |

(56) References Cited

U.S. PATENT DOCUMENTS

| | | | |
|---|---|---|---|
| 9,278,010 | B2 | 3/2016 | Gibson et al. |
| 9,283,048 | B2 | 3/2016 | Kostrzewski et al. |
| 9,289,221 | B2 | 3/2016 | Gelaude et al. |
| 9,289,270 | B2 | 3/2016 | Gielen et al. |
| 9,295,482 | B2 | 3/2016 | Fitz et al. |
| 9,295,497 | B2 | 3/2016 | Schoenefeld et al. |
| 9,295,561 | B2 | 3/2016 | Ball et al. |
| 9,301,768 | B2 | 4/2016 | Buza et al. |
| 9,308,050 | B2 | 4/2016 | Kostrzewski et al. |
| 9,308,091 | B2 | 4/2016 | Lang |
| 9,314,275 | B2 | 4/2016 | Clement et al. |
| 9,314,343 | B2 | 4/2016 | Parisi et al. |
| 9,320,547 | B2 | 4/2016 | Augostino |
| 9,320,604 | B2 | 4/2016 | Miles et al. |
| 9,326,780 | B2 | 5/2016 | Wong et al. |
| 9,339,277 | B2 | 5/2016 | Jansen et al. |
| 9,345,492 | B2 | 5/2016 | Stein et al. |
| 9,358,051 | B2 | 6/2016 | Sournac et al. |
| 9,358,130 | B2 | 6/2016 | Livorsi et al. |
| 9,358,136 | B2 | 6/2016 | Stein et al. |
| 9,364,370 | B2 | 6/2016 | Kuhnel |
| 9,381,085 | B2 | 7/2016 | Axelson, Jr. et al. |
| 9,387,015 | B2 | 7/2016 | Taylor |
| 9,392,953 | B1 | 7/2016 | Gharib |
| 9,393,052 | B2 | 7/2016 | Berg et al. |
| 9,398,962 | B2 | 7/2016 | Steinberg |
| 9,402,726 | B2 | 8/2016 | Linderman et al. |
| 9,408,615 | B2 | 8/2016 | Fitz et al. |
| 9,408,642 | B2 | 8/2016 | Wong et al. |
| 9,408,698 | B2 | 8/2016 | Miles et al. |
| 9,414,940 | B2 | 8/2016 | Stein et al. |
| 9,433,443 | B2 | 9/2016 | Montello et al. |
| 9,439,659 | B2 | 9/2016 | Schoenefeld et al. |
| 9,439,767 | B2 | 9/2016 | Bojarski et al. |
| 9,439,781 | B2 | 9/2016 | Gibson |
| 9,445,913 | B2 | 9/2016 | Donner et al. |
| 9,452,022 | B2 | 9/2016 | McIntosh et al. |
| 9,452,023 | B2 | 9/2016 | Boillot et al. |
| 9,452,050 | B2 | 9/2016 | Miles et al. |
| 9,452,064 | B2 | 9/2016 | Trautwein et al. |
| 9,468,436 | B2 | 10/2016 | Groiso |
| 9,468,502 | B2 | 10/2016 | Wiebe, III et al. |
| 9,491,415 | B2 | 11/2016 | Deitz et al. |
| 9,492,183 | B2 | 11/2016 | Wilkinson et al. |
| 9,495,483 | B2 | 11/2016 | Steines et al. |
| 9,495,509 | B2 | 11/2016 | Amiot et al. |
| 9,498,260 | B2 | 11/2016 | Funk et al. |
| 9,504,502 | B2 | 11/2016 | Kuiper et al. |
| 9,510,771 | B1 | 12/2016 | Finley et al. |
| 9,510,864 | B2 | 12/2016 | Devito |
| 9,517,134 | B2 | 12/2016 | Lang |
| 9,517,143 | B2 | 12/2016 | Prevost et al. |
| 9,526,514 | B2 | 12/2016 | Kelley et al. |
| 9,532,730 | B2 | 1/2017 | Wasielewski |
| 9,539,031 | B2 | 1/2017 | Fauth |
| 9,539,116 | B2 | 1/2017 | Claypool et al. |
| 9,539,760 | B2 | 1/2017 | Stahl et al. |
| 9,547,897 | B2 | 1/2017 | Parent et al. |
| 9,549,782 | B2 | 1/2017 | Park et al. |
| 9,554,411 | B1 | 1/2017 | Hall et al. |
| 9,554,910 | B2 | 1/2017 | Vanasse et al. |
| 9,561,115 | B2 | 2/2017 | Elahinia et al. |
| 9,566,075 | B2 | 2/2017 | Carroll et al. |
| 9,579,043 | B2 | 2/2017 | Chien et al. |
| 9,585,597 | B2 | 3/2017 | McCaulley et al. |
| 9,597,096 | B2 | 3/2017 | Aghazadeh |
| 9,597,156 | B2 | 3/2017 | Amiot et al. |
| 9,603,613 | B2 | 3/2017 | Schoenefeld et al. |
| 9,603,623 | B2 | 3/2017 | Brooks et al. |
| 9,603,711 | B2 | 3/2017 | Bojarski et al. |
| 9,610,086 | B2 | 4/2017 | Park et al. |
| 9,615,834 | B2 | 4/2017 | Agnihotri et al. |
| 9,622,712 | B2 | 4/2017 | Munro et al. |
| 9,629,723 | B2 | 4/2017 | Parisi et al. |
| 9,636,181 | B2 | 5/2017 | Isaacs |
| 9,642,633 | B2 | 5/2017 | Frey et al. |
| 9,649,170 | B2 | 5/2017 | Park et al. |
| 9,655,729 | B2 | 5/2017 | Parisi et al. |
| 9,662,214 | B2 | 5/2017 | Li et al. |
| 9,668,748 | B2 | 6/2017 | McKinnon et al. |
| 9,668,873 | B2 | 6/2017 | Winslow et al. |
| 9,675,471 | B2 | 6/2017 | Bojarski et al. |
| 9,693,831 | B2 | 7/2017 | Mosnier et al. |
| 9,715,563 | B1 | 7/2017 | Schroeder |
| 9,757,072 | B1 | 9/2017 | Urbalejo |
| 9,782,228 | B2 | 10/2017 | Mosnier et al. |
| 9,788,966 | B2 | 10/2017 | Steinberg |
| 9,827,109 | B2 | 11/2017 | Steinberg |
| 9,848,922 | B2 | 12/2017 | Tohmeh et al. |
| 9,968,408 | B1 | 5/2018 | Casey et al. |
| 9,987,048 | B2 | 6/2018 | Mosnier et al. |
| 9,993,177 | B2 | 6/2018 | Chien et al. |
| 10,010,426 | B2 | 7/2018 | Kuiper et al. |
| 10,045,824 | B2 | 8/2018 | Mosnier et al. |
| 10,052,135 | B2 | 8/2018 | Berg et al. |
| 10,064,743 | B2 | 9/2018 | Funk et al. |
| 10,098,671 | B2 | 10/2018 | Augostino |
| 10,188,480 | B2 | 1/2019 | Scholl et al. |
| 10,201,320 | B2 | 2/2019 | Saget et al. |
| 10,219,865 | B2 | 3/2019 | Jansen et al. |
| 10,292,770 | B2 | 5/2019 | Ryan et al. |
| 10,314,657 | B2 | 6/2019 | Mosnier et al. |
| 10,318,655 | B2 | 6/2019 | Mosnier et al. |
| 10,413,365 | B1 | 9/2019 | Mosnier et al. |
| 10,420,615 | B1 | 9/2019 | Mosnier et al. |
| 10,433,893 | B1 | 10/2019 | Scholl et al. |
| 10,433,912 | B1 | 10/2019 | Mosnier et al. |
| 10,433,913 | B2 | 10/2019 | Mosnier et al. |
| 10,441,363 | B1 | 10/2019 | Mosnier et al. |
| 10,456,211 | B2 | 10/2019 | McAfee |
| 10,463,433 | B2 | 11/2019 | Turner et al. |
| 2002/0035321 | A1 | 3/2002 | Bucholz et al. |
| 2002/0038118 | A1 | 3/2002 | Shoham |
| 2002/0045812 | A1 | 4/2002 | Ben-Haim et al. |
| 2002/0103432 | A1 | 8/2002 | Kawchuk |
| 2003/0191383 | A1 | 10/2003 | Ben-Haim et al. |
| 2003/0204189 | A1 | 10/2003 | Cragg |
| 2004/0120781 | A1 | 6/2004 | Luca et al. |
| 2004/0143243 | A1 | 7/2004 | Wahrburg |
| 2004/0152972 | A1 | 8/2004 | Hunter |
| 2004/0167637 | A1 | 8/2004 | Biscup |
| 2004/0171924 | A1 | 9/2004 | Mire et al. |
| 2004/0172020 | A1 | 9/2004 | Beaurain et al. |
| 2004/0215190 | A1 | 10/2004 | Nguyen et al. |
| 2004/0243148 | A1 | 12/2004 | Wasielewski |
| 2004/0267279 | A1 | 12/2004 | Casutt et al. |
| 2005/0149050 | A1 | 7/2005 | Stifter et al. |
| 2005/0177239 | A1 | 8/2005 | Steinberg |
| 2005/0182320 | A1 | 8/2005 | Stifter et al. |
| 2005/0182454 | A1 | 8/2005 | Gharib et al. |
| 2005/0203531 | A1 | 9/2005 | Lakin et al. |
| 2005/0203532 | A1 | 9/2005 | Ferguson |
| 2005/0262911 | A1 | 12/2005 | Dankowicz et al. |
| 2006/0015018 | A1 | 1/2006 | Jutras et al. |
| 2006/0015030 | A1 | 1/2006 | Poulin et al. |
| 2006/0036259 | A1 | 2/2006 | Carl et al. |
| 2006/0069324 | A1 | 3/2006 | Block et al. |
| 2006/0074431 | A1 | 4/2006 | Sutton et al. |
| 2006/0136058 | A1 | 6/2006 | Pietrzak |
| 2006/0142657 | A1 | 6/2006 | Quaid et al. |
| 2006/0285991 | A1 | 12/2006 | McKinley |
| 2006/0287627 | A1 | 12/2006 | Johnson |
| 2007/0021682 | A1 | 1/2007 | Gharib et al. |
| 2007/0118243 | A1 | 5/2007 | Schroeder et al. |
| 2007/0225731 | A1 | 9/2007 | Couture et al. |
| 2008/0058945 | A1 | 3/2008 | Hajaj et al. |
| 2008/0108991 | A1 | 5/2008 | von Jako |
| 2008/0177203 | A1 | 7/2008 | von Jako |
| 2008/0255575 | A1 | 10/2008 | Justis et al. |
| 2008/0281332 | A1 | 11/2008 | Taylor |
| 2009/0024164 | A1 | 1/2009 | Neubardt |
| 2009/0076615 | A1 | 3/2009 | Duggal et al. |
| 2009/0157083 | A1 | 6/2009 | Park et al. |
| 2009/0194206 | A1 | 8/2009 | Jeon et al. |

(56) References Cited

U.S. PATENT DOCUMENTS

| | | |
|---|---|---|
| 2009/0204159 A1 | 8/2009 | Justis et al. |
| 2009/0248080 A1 | 10/2009 | Wilcox et al. |
| 2009/0249851 A1 | 10/2009 | Isaacs |
| 2009/0254326 A1 | 10/2009 | Isaacs |
| 2010/0042157 A1 | 2/2010 | Trieu |
| 2010/0100011 A1 | 4/2010 | Roche |
| 2010/0191071 A1* | 7/2010 | Anderson ............ G16H 50/50 703/11 |
| 2010/0191088 A1 | 7/2010 | Anderson et al. |
| 2010/0217270 A1 | 8/2010 | Polinski et al. |
| 2010/0217336 A1 | 8/2010 | Crawford et al. |
| 2011/0004309 A9 | 1/2011 | Holm |
| 2011/0071802 A1 | 3/2011 | Bojarski et al. |
| 2011/0118740 A1 | 5/2011 | Rabiner et al. |
| 2011/0172566 A1 | 7/2011 | Kawchuk |
| 2011/0214279 A1 | 9/2011 | Park et al. |
| 2011/0224796 A1 | 9/2011 | Weiland et al. |
| 2011/0257653 A1 | 10/2011 | Hughes et al. |
| 2011/0257657 A1 | 10/2011 | Turner et al. |
| 2011/0295159 A1 | 12/2011 | Shachar et al. |
| 2011/0306873 A1 | 12/2011 | Shenai et al. |
| 2012/0022357 A1 | 1/2012 | Chang et al. |
| 2012/0027261 A1 | 2/2012 | Frank et al. |
| 2012/0035611 A1 | 2/2012 | Kave |
| 2012/0123301 A1 | 5/2012 | Connor et al. |
| 2012/0143090 A1 | 6/2012 | Hay et al. |
| 2012/0150243 A9 | 6/2012 | Crawford et al. |
| 2012/0172884 A1 | 7/2012 | Zheng et al. |
| 2012/0203289 A1 | 8/2012 | Beerens et al. |
| 2013/0079678 A1 | 3/2013 | Stein et al. |
| 2013/0079679 A1 | 3/2013 | Roche et al. |
| 2013/0079790 A1 | 3/2013 | Stein et al. |
| 2013/0131486 A1 | 5/2013 | Copf et al. |
| 2013/0211531 A1 | 8/2013 | Steines et al. |
| 2013/0245631 A1 | 9/2013 | Bettenga |
| 2013/0253599 A1 | 9/2013 | Gorek et al. |
| 2013/0268007 A1 | 10/2013 | Rezach et al. |
| 2013/0303883 A1 | 11/2013 | Zehavi et al. |
| 2013/0345718 A1 | 12/2013 | Crawford et al. |
| 2014/0058407 A1 | 2/2014 | Tsekos et al. |
| 2014/0100579 A1 | 4/2014 | Kelman et al. |
| 2014/0135658 A1 | 5/2014 | Hladio et al. |
| 2014/0180415 A1 | 6/2014 | Koss |
| 2014/0194889 A1 | 7/2014 | Chang et al. |
| 2014/0228670 A1 | 8/2014 | Justis et al. |
| 2014/0228860 A1 | 8/2014 | Steines et al. |
| 2014/0244220 A1 | 8/2014 | McKinnon et al. |
| 2014/0257402 A1 | 9/2014 | Barsoum |
| 2014/0272881 A1 | 9/2014 | Barsoum |
| 2014/0277149 A1 | 9/2014 | Rooney et al. |
| 2014/0296860 A1 | 10/2014 | Stein et al. |
| 2014/0303672 A1 | 10/2014 | Tran et al. |
| 2014/0316468 A1 | 10/2014 | Keiser et al. |
| 2015/0057756 A1 | 2/2015 | Lang et al. |
| 2015/0066145 A1 | 3/2015 | Rogers et al. |
| 2015/0080901 A1 | 3/2015 | Stein |
| 2015/0081029 A1 | 3/2015 | Bojarski et al. |
| 2015/0088030 A1 | 3/2015 | Taylor |
| 2015/0100066 A1 | 4/2015 | Kostrzewski et al. |
| 2015/0100091 A1 | 4/2015 | Tohmeh et al. |
| 2015/0105782 A1 | 4/2015 | D'Lima et al. |
| 2015/0127055 A1 | 5/2015 | Dvorak et al. |
| 2015/0150646 A1 | 6/2015 | Pryor et al. |
| 2015/0164657 A1 | 6/2015 | Miles et al. |
| 2015/0182292 A1 | 7/2015 | Hladio et al. |
| 2015/0223900 A1 | 8/2015 | Wiebe, III et al. |
| 2015/0245844 A1 | 9/2015 | Kennedy et al. |
| 2015/0250597 A1 | 9/2015 | Lang et al. |
| 2015/0265291 A1 | 9/2015 | Wilkinson |
| 2015/0305878 A1 | 10/2015 | O'Neil et al. |
| 2015/0305891 A1 | 10/2015 | Bergin et al. |
| 2015/0313723 A1 | 11/2015 | Jansen et al. |
| 2015/0328004 A1 | 11/2015 | Mafhouz |
| 2015/0366630 A1 | 12/2015 | Gorek et al. |
| 2016/0000571 A1 | 1/2016 | Mahfouz |
| 2016/0007983 A1 | 1/2016 | Frey et al. |
| 2016/0015465 A1 | 1/2016 | Steines et al. |
| 2016/0022176 A1 | 1/2016 | Le Huec et al. |
| 2016/0022370 A1 | 1/2016 | Pavlovskaia et al. |
| 2016/0038161 A1 | 2/2016 | Gibson |
| 2016/0038238 A1 | 2/2016 | Kostrzewski et al. |
| 2016/0038242 A1 | 2/2016 | Lo Iacono et al. |
| 2016/0038293 A1 | 2/2016 | Slamin et al. |
| 2016/0038307 A1 | 2/2016 | Bettenga |
| 2016/0045230 A1 | 2/2016 | Lowery et al. |
| 2016/0045317 A1 | 2/2016 | Lang et al. |
| 2016/0045326 A1 | 2/2016 | Hansen et al. |
| 2016/0058320 A1 | 3/2016 | Chien et al. |
| 2016/0058523 A1 | 3/2016 | Chien et al. |
| 2016/0074052 A1 | 3/2016 | Keppler et al. |
| 2016/0074202 A1 | 3/2016 | Reed et al. |
| 2016/0081754 A1 | 3/2016 | Kostrzewski et al. |
| 2016/0095710 A1 | 4/2016 | Juszczyk et al. |
| 2016/0100907 A1 | 4/2016 | Gomes |
| 2016/0106483 A1 | 4/2016 | Mayer et al. |
| 2016/0128847 A1 | 5/2016 | Kurtaliaj et al. |
| 2016/0143744 A1 | 5/2016 | Bojarski et al. |
| 2016/0157751 A1 | 6/2016 | Mahfouz |
| 2016/0199101 A1 | 7/2016 | Sharifi-Mehr et al. |
| 2016/0228192 A1 | 8/2016 | Jansen et al. |
| 2016/0235480 A1 | 8/2016 | Scholl et al. |
| 2016/0235493 A1 | 8/2016 | LeBoeuf, II et al. |
| 2016/0242819 A1 | 8/2016 | Simpson et al. |
| 2016/0242857 A1 | 8/2016 | Scholl |
| 2016/0242934 A1 | 8/2016 | van der Walt et al. |
| 2016/0256279 A1 | 9/2016 | Sanders et al. |
| 2016/0256285 A1 | 9/2016 | Jansen |
| 2016/0262800 A1 | 9/2016 | Scholl et al. |
| 2016/0262895 A1 | 9/2016 | Shea et al. |
| 2016/0270802 A1 | 9/2016 | Fang et al. |
| 2016/0270931 A1 | 9/2016 | Trieu |
| 2016/0274571 A1 | 9/2016 | Lavallee et al. |
| 2016/0283676 A1 | 9/2016 | Lyon et al. |
| 2016/0287395 A1 | 10/2016 | Khalili et al. |
| 2016/0296285 A1 | 10/2016 | Chaoui et al. |
| 2016/0310221 A1 | 10/2016 | Bar et al. |
| 2016/0331417 A1 | 11/2016 | Trautwein et al. |
| 2016/0354009 A1 | 12/2016 | Schroeder |
| 2016/0354161 A1 | 12/2016 | Deitz |
| 2016/0360997 A1 | 12/2016 | Yadav et al. |
| 2017/0000568 A1 | 1/2017 | O'Neil et al. |
| 2017/0007145 A1 | 1/2017 | Gharib et al. |
| 2017/0007328 A1 | 1/2017 | Cattin et al. |
| 2017/0007408 A1 | 1/2017 | Fitz et al. |
| 2017/0027590 A1 | 2/2017 | Amiot et al. |
| 2017/0027617 A1 | 2/2017 | Strnad |
| 2017/0035580 A1 | 2/2017 | Murphy |
| 2017/0056179 A1 | 3/2017 | Lorio |
| 2017/0056196 A1 | 3/2017 | Kuiper et al. |
| 2017/0071503 A1 | 3/2017 | Wasielewski |
| 2017/0119472 A1 | 5/2017 | Herrmann et al. |
| 2017/0132389 A1 | 5/2017 | McCaulley et al. |
| 2017/0135706 A1 | 5/2017 | Frey et al. |
| 2017/0135707 A9 | 5/2017 | Frey et al. |
| 2017/0135770 A1 | 5/2017 | Scholl et al. |
| 2017/0143426 A1 | 5/2017 | Isaacs et al. |
| 2017/0143494 A1 | 5/2017 | Mahfouz |
| 2017/0143502 A1 | 5/2017 | Yadin et al. |
| 2017/0156798 A1 | 6/2017 | Wasielewski |
| 2017/0189121 A1 | 7/2017 | Frasier et al. |
| 2017/0231709 A1 | 8/2017 | Gupta et al. |
| 2017/0252107 A1 | 9/2017 | Turner et al. |
| 2017/0273718 A1 | 9/2017 | Metzger et al. |
| 2017/0323037 A1 | 11/2017 | Schroeder |
| 2017/0360493 A1 | 12/2017 | Zucker et al. |
| 2018/0178148 A1 | 6/2018 | Mazor et al. |
| 2018/0256067 A1 | 9/2018 | Chien et al. |
| 2018/0289396 A1 | 10/2018 | McGahan et al. |
| 2018/0295584 A1 | 10/2018 | Gliner et al. |
| 2018/0301213 A1 | 10/2018 | Zehavi et al. |
| 2018/0303552 A1 | 10/2018 | Ryan et al. |
| 2018/0310993 A1 | 11/2018 | Hobeika et al. |
| 2018/0349519 A1 | 12/2018 | Schroeder |
| 2019/0015136 A1 | 1/2019 | Kraemer |

(56) References Cited

U.S. PATENT DOCUMENTS

| | | |
|---|---|---|
| 2019/0046269 A1 | 2/2019 | Hedblom et al. |
| 2019/0046287 A1 | 2/2019 | Fallin et al. |
| 2019/0059951 A1 | 2/2019 | Barrus |
| 2019/0060086 A1 | 2/2019 | Krause et al. |
| 2019/0083144 A1 | 3/2019 | Sharifi-Mehr et al. |
| 2019/0103190 A1 | 4/2019 | Schmidt et al. |
| 2019/0110819 A1 | 4/2019 | Triplett et al. |
| 2019/0117278 A1 | 4/2019 | Chin |
| 2019/0122364 A1 | 4/2019 | Zhang et al. |
| 2019/0130639 A1* | 5/2019 | Boyce ............ G06V 10/28 |
| 2019/0142599 A1 | 5/2019 | Thibodeau |
| 2019/0167314 A1 | 6/2019 | Mosnier et al. |
| 2019/0201013 A1 | 7/2019 | Siccardi et al. |
| 2019/0201155 A1 | 7/2019 | Gupta et al. |
| 2019/0209212 A1 | 7/2019 | Scholl et al. |
| 2019/0223916 A1 | 7/2019 | Barrus et al. |
| 2019/0231443 A1 | 8/2019 | McGinley et al. |
| 2019/0231557 A1 | 8/2019 | Sutterlin, III et al. |
| 2019/0239935 A1 | 8/2019 | Willis et al. |
| 2019/0247100 A1 | 8/2019 | Mundis, Jr. et al. |
| 2019/0254769 A1 | 8/2019 | Scholl et al. |
| 2019/0262015 A1 | 8/2019 | Siccardi et al. |
| 2019/0269463 A1 | 9/2019 | Mosnier et al. |
| 2019/0343587 A1 | 11/2019 | Mosnier et al. |
| 2019/0362028 A1 | 11/2019 | Mosnier et al. |
| 2019/0380782 A1 | 12/2019 | McAfee et al. |
| 2020/0060768 A1 | 2/2020 | Mosnier et al. |
| 2020/0121394 A1 | 4/2020 | Mosnier et al. |

FOREIGN PATENT DOCUMENTS

| | | |
|---|---|---|
| AU | 2019200740 A1 | 2/2019 |
| AU | 2019200888 A1 | 2/2019 |
| AU | 2019203557 A1 | 6/2019 |
| CA | 2872845 A1 | 11/2013 |
| CA | 2927955 A1 | 4/2014 |
| CN | 1816134 A | 8/2006 |
| CN | 102805677 A | 12/2012 |
| CN | 104127229 A | 11/2014 |
| CN | 205073000 U | 3/2016 |
| CN | 103892953 B | 5/2016 |
| CN | 104323843 B | 1/2017 |
| CN | 104434287 B | 1/2017 |
| CN | 105078555 B | 9/2018 |
| EP | 1 570 781 A1 | 9/2005 |
| EP | 2 053 580 A1 | 4/2009 |
| EP | 2 749 235 A1 | 7/2014 |
| EP | 2 754 419 A2 | 7/2014 |
| EP | 2 496 183 B1 | 9/2015 |
| EP | 3 000 443 A2 | 3/2016 |
| EP | 2 608 749 B1 | 8/2016 |
| EP | 2 403 434 B1 | 4/2017 |
| EP | 3 431 032 A1 | 1/2019 |
| FR | 1358988 A | 4/1964 |
| FR | 1360208 A | 5/1964 |
| JP | 2016-537036 A | 12/2016 |
| JP | 2016-540610 A | 12/2016 |
| SU | 1497721 A1 | 7/1989 |
| SU | 1704102 A1 | 1/1992 |
| WO | 199855038 A1 | 12/1998 |
| WO | 00/53077 A2 | 9/2000 |
| WO | 04/017836 A2 | 3/2004 |
| WO | 04/030559 A1 | 4/2004 |
| WO | 04/089224 A2 | 10/2004 |
| WO | 04/111948 A2 | 12/2004 |
| WO | 05/074368 A2 | 8/2005 |
| WO | 06/075331 A2 | 7/2006 |
| WO | 06/084193 A2 | 8/2006 |
| WO | 07/035925 A2 | 3/2007 |
| WO | 07/038290 A2 | 4/2007 |
| WO | 08/002588 A2 | 1/2008 |
| WO | 08/079546 A2 | 7/2008 |
| WO | 08/124079 A1 | 10/2008 |
| WO | 09/119181 A1 | 10/2009 |
| WO | 09/124245 A1 | 10/2009 |
| WO | 10/044880 A1 | 4/2010 |
| WO | 10/064234 A2 | 6/2010 |
| WO | 10/121147 A1 | 10/2010 |
| WO | 10/147972 A1 | 12/2010 |
| WO | 11/021192 A1 | 2/2011 |
| WO | 12/012863 A1 | 2/2012 |
| WO | 12/113030 A1 | 8/2012 |
| WO | 12/131660 A1 | 10/2012 |
| WO | 13/003435 A1 | 1/2013 |
| WO | 14/191790 A1 | 12/2014 |
| WO | 15/040552 A1 | 3/2015 |
| WO | 15/054543 A1 | 4/2015 |
| WO | 15/056131 A1 | 4/2015 |
| WO | 15/079011 A1 | 6/2015 |
| WO | 15/089118 A1 | 6/2015 |
| WO | 15/185219 A1 | 12/2015 |
| WO | 15/195843 A2 | 12/2015 |
| WO | 15/200720 A2 | 12/2015 |
| WO | 16/012726 A1 | 1/2016 |
| WO | 16/019424 A1 | 2/2016 |
| WO | 16/019425 A1 | 2/2016 |
| WO | 16/019426 A1 | 2/2016 |
| WO | 16/26053 A1 | 2/2016 |
| WO | 16/032875 A1 | 3/2016 |
| WO | 16/044352 A1 | 3/2016 |
| WO | 16/048800 A1 | 3/2016 |
| WO | 16/088130 A1 | 6/2016 |
| WO | 16/094826 A1 | 6/2016 |
| WO | 16/102026 A1 | 6/2016 |
| WO | 16/137347 A1 | 9/2016 |
| WO | 16/148675 A1 | 9/2016 |
| WO | 16/165030 A1 | 10/2016 |
| WO | 17/001851 A1 | 1/2017 |
| WO | 17/039596 A1 | 3/2017 |
| WO | 17/064719 A1 | 4/2017 |
| WO | 17/066518 A1 | 4/2017 |
| WO | 17/077356 A1 | 5/2017 |
| WO | 17/079655 A2 | 5/2017 |
| WO | WO-2017074890 A1 * | 5/2017 ............ G06T 7/11 |
| WO | 17/127838 A1 | 7/2017 |
| WO | 17/151949 A1 | 9/2017 |
| WO | 17/221257 A1 | 12/2017 |
| WO | 18/045086 A1 | 3/2018 |
| WO | 18/055494 A1 | 3/2018 |
| WO | 18/055518 A1 | 3/2018 |
| WO | 18/078636 A1 | 5/2018 |
| WO | 18/087758 A1 | 5/2018 |
| WO | 18/131044 A1 | 7/2018 |
| WO | 18/131045 A1 | 7/2018 |
| WO | 18/183314 A1 | 10/2018 |
| WO | 18/185755 A1 | 10/2018 |
| WO | 18/193316 A2 | 10/2018 |
| WO | 18/193317 A1 | 10/2018 |
| WO | 18/203100 A1 | 11/2018 |
| WO | 18/203101 A1 | 11/2018 |
| WO | 19/014452 A1 | 1/2019 |
| WO | 2019036039 A2 | 2/2019 |
| WO | 2019043426 A1 | 3/2019 |
| WO | 2019068085 A1 | 4/2019 |
| WO | 2019070729 A1 | 4/2019 |
| WO | 2019118844 A1 | 6/2019 |
| WO | 2019140240 A1 | 7/2019 |

OTHER PUBLICATIONS

Continue item U] Media LLC. https://doi.org/10.1007/s00198-011-1604-3 (Year: 2011).*

Damopoulos, D., Glocker, B., Zheng, G. (2018). Automatic Localization of the Lumbar Vertebral Landmarks in CT Images with Context Features. In: Glocker, B., Yao, J., Vrtovec, T., Frangi, A., Zheng, G. (eds) Computational Methods and Clinical Applications in Musculoskeletal Imaging. MSKI 2017. Lecture (Year: 2018).*

Continue item W] Notes in Computer Science, vol. 10734. Springer, Cham. https://doi.org/10.1007/978-3-319-74113-0_6. (Year: 2018).*

Abe et al. "Scoliosis corrective force estimation from the implanted rod deformation using 3 D FEM analysis", 2015, Scoliosis 10(Suppl 2):52, 6 pages.

(56) References Cited

OTHER PUBLICATIONS

Aubin et al. "Preoperative Planning Simulator for Spinal Deformity Surgeries", Spine 2008, 33(20):2143-2152.

Barton et al., Mar./Apr. 2016, Early experience and initial outcomes with patient-specific spine rods for adult spinal deformity, Trending in Orthopedics, 39(2):79-86.

Fiere et al., Jul. 2016, 40. Preoperative planning and patient-specific rods for surgical treatment of thoracolumbar sagittal imbalance, in Surgery of the Spine and Spinal Cord. A Neurosurgical Approach, Van de Kalft ed., Springer International Publishing, Switzerland, pp. 645-662.

Foroozandeh et al., Summer 2012, 3D reconstruction using cubic Bezier spline curves and active contours (case study), Iranian Journal of Medical Physics, 9(3):169-176.

Galbusera et al., Feb. 2019, Artificial intelligence and machine learning in spine research, JOR Spine, 2:E1044, 20 pp.

Grove, 2011, Heterogeneous modeling of medical image data using B-spline functions, doctoral dissertation, Department of Computer Science and Engineering, University of South Florida, 212 pp.

Azarus, Jun. 21, 2013, An introduction to splines; 29 pp.

Li et al., 2009, Modeling and measurement of 3D deformation of scoliotic spine using 2D x-ray images, Lecture Notes in Computer Science; 8 pp.

Lin, Sep. 17-21, 2003, The simplified spine modeling by 3-D Bezier curve based on the orthogonal spinal radiographic images, Proceedings of the 25th Annual International Conference of the IEEE EMBS, Cancun, Mexico, pp. 944-946.

Pasha et al., 2018, Data-driven classification of the 3D spinal curve in adolescent idiopathic scoliosis with an applications in surgical outcome prediction, Scientific Reports, 8:16296, 10 pp.

Poredos et al.; 2015; Determination of the human spine curve based on laser triangulation, BMC Medical Imaging 15(2):1-11.

Prautzsch et al., Mar. 26, 2001, Bezier-and B-spline techniques; 58 pp.

Ratnakar et al. 2011, Predicting thoracic spinal postures in finite element model with Bezier technique, Ircobe Conference 2011, IRC-11-57, 4 pp.

Reinshagen et al. "A novel minimally invasive technique for lumbar decompression, realignment, and navigated interbody fusion"; J Clin Neurosci. 2015, 22(9):1484-1490; XP055503028.

Rickert et al., "Posterior lumbar interbody fusion implants", Orthopaede, Springer Verlag, Berlin, DE vol. 44, No. 2 dated Jan. 28, 2015 pp. 162-169.

Solla et al.; Mar. 2019, Patient-specific rods for surgical correction of sagittal imbalance in adults: Technical aspects and preliminary results, Clin Spine Surg, 32(2), 7 pp.

Spontech Medical AG Vertaplan—die Software fur Wirbelsaulenchirurgen, Aug. 29, 2013 Retrieved from the Internet: URL: https://www.youtube.com/watch?v=q0qhW1T1cp8 in 1 page.

* cited by examiner

SYSTEMS AND METHODS FOR MEDICAL IMAGE ANALYSIS

CROSS-REFERENCE TO RELATED APPLICATIONS

The present application claims priority to and the benefit of U.S. Patent Ser. No. 62/953,677, which is entitled "Systems, Devices, And Methods For Medical Image Analysis" and was filed on Dec. 23, 2020. The content of which are incorporated herein in its entirety.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation, and exercise can be effective, however, may fail to relieve the symptoms associated with these disorders. Surgical treatment of these spinal disorders includes correction, fusion, fixation, discectomy, laminectomy, and/or implantable prosthetics. As part of these surgical treatments, spinal constructs, which include implants such as bone fasteners, connectors, plates, and vertebral rods are often used to provide stability to a treated region. These implants can redirect stresses away from a damaged or defective region while healing takes place to restore proper alignment and generally support the vertebral members. The particular curvature, length and/or other parameters of the implants can be a key factor in obtaining successful results from surgery.

SUMMARY

The present disclosure relates to implementing systems and methods for medical treatment. The methods may comprise performing the following operations by a computing device: causing an imaging device to capture a medical image; receiving information identifying at least one first point (e.g., a first vertebrae endpoint) on a body part (e.g., a spine) shown in a medical image; overlaying a first mark on the medical image for the first point; generating a spline (e.g., a piecewise polynomial curve) based on the first mark and/or machine learned model(s) (e.g., defining possible structure(s) of the body part); overlaying a second mark for the spline on the medical image; identifying a location of at least one second point (e.g., a second different vertebrae endpoint) on the body part (e.g., the spine) shown in the medical image based on the first mark, the second mark, machine learned model(s) and/or contents of a scientific database; overlaying a third mark for the second point on the medical image; address an error in at least one characteristic of the third mark; and/or using at least the third mark to facilitate the medical treatment of an individual whose body part is shown in the medical image.

In some scenarios, the second mark comprises a curved line that (i) extends between a mid-point of the first mark and a mid-point of another mark, and (ii) extends along a centerline of the body part. The error is addressed by: analyzing differences in gray levels for pixels residing within a given area surrounding an end of the third mark to determine a precise location of an object corner (e.g., a vertebrae corner); and modifying at least one of a shape of the third mark, a size of the third mark and a location of the third mark relative to the medical image in accordance with results of the analyzing.

The present disclosure relates also relates to a system comprising a processor and a non-transitory computer-readable storage medium. The non-transitory computer-readable storage medium comprises programming instructions that are configured to cause the processor to implement the above-described method for medical treatment.

The foregoing and other objects, features and advantages of the invention will be apparent from the following more particular descriptions of exemplary embodiments of the invention as illustrated in the accompanying drawings wherein like reference numbers generally represent like parts of the disclosure.

BRIEF DESCRIPTION OF DRAWINGS

The following drawings are illustrative of particular embodiments of the present disclosure and therefore do not limit the scope of the present disclosure. The drawings are not to scale and are intended for use in conjunction with the explanations in the following detailed description.

DETAILED DESCRIPTION

The following discussion omits or only briefly describes certain conventional features related to surgical systems for treating the spine, which are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure generally relate to implementing systems and methods for analyzing medical images. The methods involve: causing an imaging device to capture a medical image; receiving information identifying at least one first point (e.g., a first vertebrae endpoint) on a body part (e.g., a spine) shown in a medical image; overlaying a first mark on the medical image for the first point; generating a spline (e.g., a piecewise polynomial curve) based on the first mark and/or machine learned model(s) (e.g., defining a possible structure of a spine); overlaying a second mark for the spline on the medical image; identifying a location of at least one second point (e.g., a second different vertebrae endpoint) on the body part (e.g., the spine) shown in the medical image based on the first mark, the second mark, machine learned model(s) and/or contents of a scientific database; overlaying a third mark for the second point on the medical image; address an error in a characteristic of the third mark; and/or using at least the third mark to facilitate the medical treatment of an individual whose body part is shown in the medical image.

Figure 1:
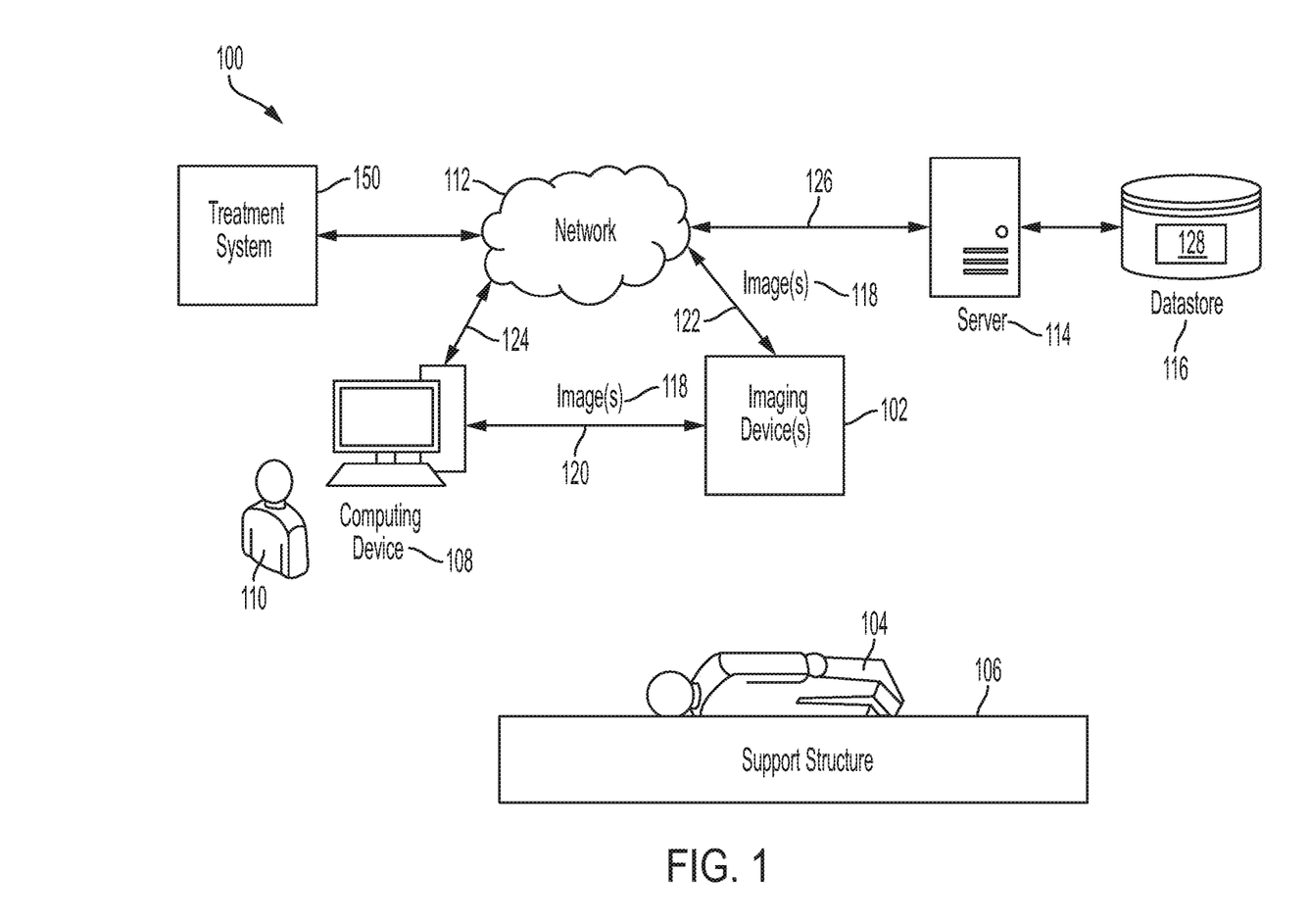
FIG. 1 provides an illustration of an illustrative system.

Referring now to FIG. 1, there is provided an illustration of an illustrative system 100. System 100 is generally configured to analyze images to detect a spine and/or a vertebrae of a patient 104. During operation, the patient 104 may be placed on a support structure 106 (e.g., table) such that imaging device(s) 102 is(are) aligned with a body part of interest (e.g., a back).

The imaging device(s) 102 can include, but is(are) not limited to, an X-ray system. The imaging device(s) 102 is(are) generally configured to capture at least one image 118 of a treatment area (e.g., at least a portion of the patient's spine). The image can include, but is not limited to, a Digital Tomosynthesis (DT) scan image, a Computed Tomography (CT) scan image, a Magnetic Resonance Imaging (MRI) image and/or a Positron Emission Tomography (PET) scan image).

The image 118 is communicated from the imaging device 102 to a computing device 108 via a communications link 120 and/or via a network 112 using communication links 122, 124. Additionally or alternatively, the image 118 is communicated from the imaging device 102 to a server 114 via network 112 using communication links 122, 126. The server 114 is configured to access a datastore 116 for reading information 128 therefrom and writing information 128 thereto. The network can include, but is not limited to, a Local Area Network (LAN), a Wide Area Network (WAN), an Intranet and/or the Internet. The communication links 120, 122, 124, 126 can be wired communication links and/or wireless communication links.

The image 118 is analyzed by the computing device 108 and/or server 114. The image analysis is generally performed automatively to detect a vertebral object and/or generate measurement data for the same. The manner in which such detection is made will become apparent as the discussion progresses. In some scenarios, the detection is achieved using anatomical knowledge and/or scientific literature to identify approximate positions of vertebrae in a given image, and then analyzing content of each approximate position to determine whether a vertebral object resides thereat.

Figure 2:
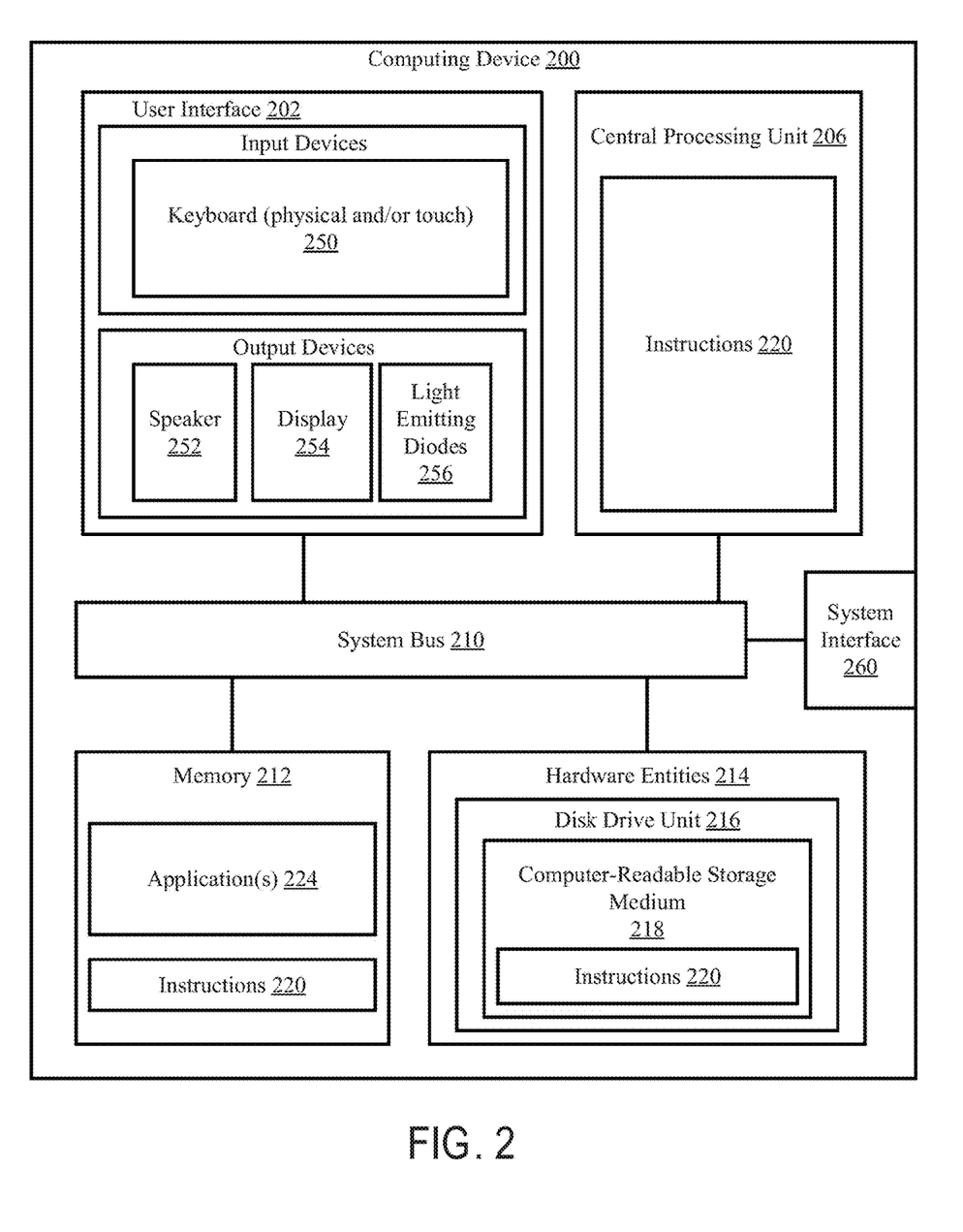
FIG. 2 provides an illustration of an illustrative computing device.

Referring now to FIG. 2, there is provided an illustration of an illustrative architecture for a computing device 200. The computing device 108 and/or server 114 of FIG. 1 is at least partially the same as or similar to computing device 200. As such, the discussion of computing device 300 is sufficient for understanding the vehicle on-board computing device 220 of FIG. 2.

Computing device 200 may include more or less components than those shown in FIG. 2. However, the components shown are sufficient to disclose an illustrative solution implementing the present solution. The hardware architecture of FIG. 2 represents one implementation of a representative computing device configured to perform medical image processing, as described herein. As such, the computing device 200 of FIG. 2 implements at least a portion of the method(s) described herein.

Some or all components of the computing device 200 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 2, the computing device 200 comprises a user interface 202, a Central Processing Unit (CPU) 206, a system bus 210, a memory 212 connected to and accessible by other portions of computing device 200 through system bus 210, a system interface 260, and hardware entities 214 connected to system bus 210. The user interface can include input devices and output devices, which facilitate user-software interactions for controlling operations of the computing device 200. The input devices include, but are not limited to, a physical and/or touch keyboard 250. The input devices can be connected to the computing device 200 via a wired or wireless connection (e.g., a Bluetooth® connection). The output devices include, but are not limited to, a speaker 252, a display 254, and/or light emitting diodes 256. Display 254 can include, but is not limited to, a Cathode Ray Tube (CRT), a Liquid Crystal Display (LCD), a plasma display and/or a touch-screen display. System interface 260 is configured to facilitate wired or wireless communications to and from external devices (e.g., network nodes such as access points, etc.).

At least some of the hardware entities 214 perform actions involving access to and use of memory 212, which can be a Random Access Memory (RAM), a disk drive, flash memory, a Compact Disc Read Only Memory (CD-ROM) and/or another hardware device that is capable of storing instructions and data. Hardware entities 214 can include a disk drive unit 216 comprising a computer-readable storage medium 218 on which is stored one or more sets of instructions 220 (e.g., software code) configured to implement one or more of the methodologies, procedures, or functions described herein. The instructions 220 can also reside, completely or at least partially, within the memory 212 and/or within the CPU 206 during execution thereof by the computing device 200. The memory 212 and the CPU 206 also can constitute machine-readable media. The term "machine-readable media", as used here, refers to a single medium or multiple media (e.g., a centralized or distributed database, and/or associated caches and servers) that store the one or more sets of instructions 220. The term "machine-readable media", as used here, also refers to any medium that is capable of storing, encoding or carrying a set of instructions 220 for execution by the computing device 200 and that cause the computing device 200 to perform any one or more of the methodologies of the present disclosure.

The methodologies of the present disclosure may be implemented at least partly by application(s) 224. The application(s) 224 may include, but are not limited to, web-enabled applications that uses text, widgets, graphics, audio, video and other media to present data and to allow interaction with data via a network (e.g., network 112 of FIG. 1). The widgets are configured to facilitate user-software interactions with computing device 200. In this regard, the widgets can include, but are not limited to, menus, windows, dialogue boxes, tool bars and/or controls (for example, radio buttons, check boxes, and/or sliding scales).

In some embodiments, one or more features of the present solution described herein can utilize a Uniform Resource Locator (URL) and/or cookies, for example for storing and/or transmitting data or user information. The URL can include a web address and/or a reference to a web resource that is stored on in a datastore (e.g., datastore 116 of FIG. 1). The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address. A Doman Name System (DNS) can look up the URL and its corresponding IP address. URLs can be references to web pages, file transfers, emails, database accesses and/or other applications. The URLs can include a sequence of characters that identify a path, domain name, a file extension, a host name, a query, a fragment, scheme, a protocol identifier, a port number, a username, a password, a flag, an object and/or a resource name. The systems disclosed herein can generate, receive, transmit, apply, parse, serialize, render, and/or perform an action on a URL.

A cookie (also referred to as an HTTP cookie, a web cookie, an internet cookie, and a browser cookie) can include data sent from a website and/or stored on the computing device 200 and/or another computing device. This data can be stored by a web browser while the user is browsing through data. The cookies can include useful information for websites to remember prior browsing information. The useful information can include, but is not limited to, a shopping cart on an online store, a clicking of buttons, login information and/or records of web pages or network resources visited in the past. Cookies can also include information that the user enters such as names, addresses, passwords, credit card information, etc. Cookies can also perform computer functions. For example, authentication cookies can be used by applications 224 (e.g., a web browser) to identify whether the user is already logged in (e.g., to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information and/or URLs.

Figure 3:
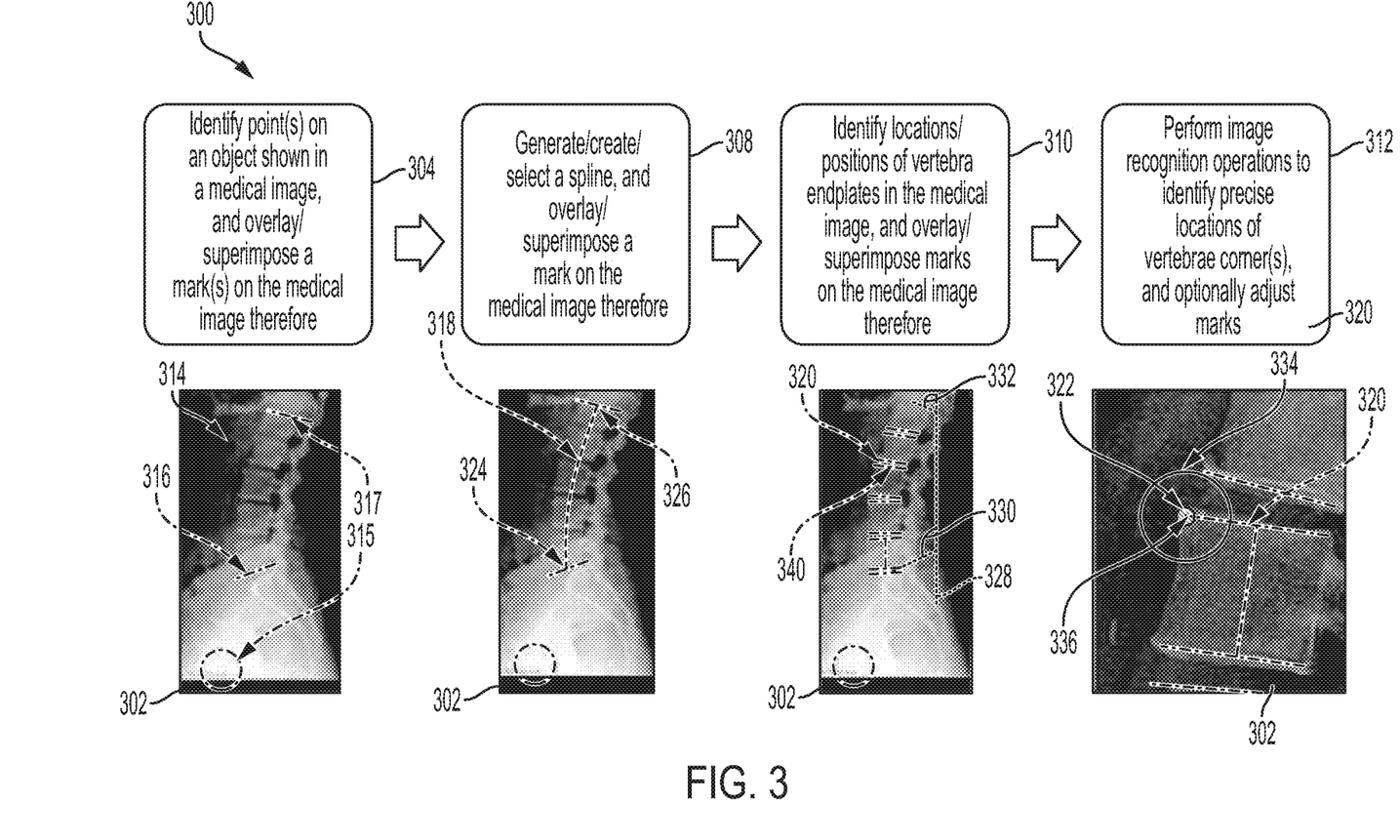
FIG. 3 provides an illustration of an illustrative process for analyzing images.

Referring now to FIG. 3, there is provided an illustration of an illustrative method 300 for analyzing a medical image 302. It should be noted that machine learned models are used in method 300 for various purposes. The manner in which the machine learned models are used will become evident as the discussion progresses. The machine learned models are generated based on medical images for a plurality of individuals. Each machine learned model represents a possible structure of a body part (e.g., a spine). In this regard, each machine learned model may define relative locations of femoral heads to vertebrae, relative locations of vertebrae to each other, dimensions of vertebrae, relative locations of vertebrae edges, angles of vertebrae edges relative to a reference line, a centerline of the spine, and a curvature of the centerline.

After the machine learned models have been generated, an individual (e.g., individual 110 of FIG. 1) of a medical practice (e.g., a doctor, a nurse, or a technician) performs a user-software action to launch a software application (e.g., software application 224 of FIG. 4) installed on a computing device (e.g., computing device 108 of FIG. 1, server 114 of FIG. 1, and/or computing device 200 of FIG. 2). The software application is generally configured to cause a medical image 302 of a patient (e.g., patient 104 of FIG. 1) to be captured by an imaging device (e.g., imaging device 102 of FIG. 1). The medical image 302 may be captured during an office visit. The medical image 302 comprises an image of a part of the patient's body (e.g., a spine).

Figure 4:
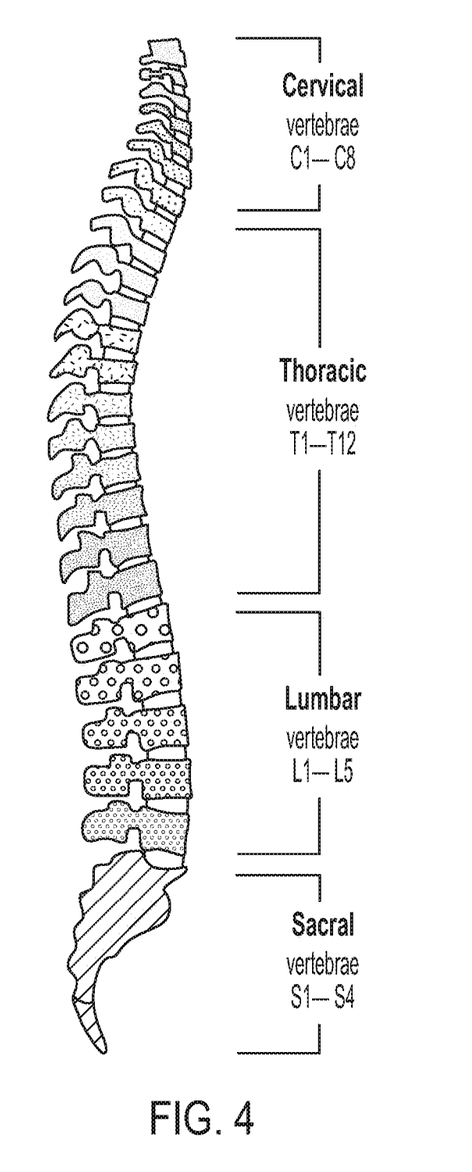
FIG. 4 provides an illustration of a spine.

Next, the medical image 302 is presented to the individual on a display (e.g., display 254 of FIG. 2) of the computing device. The individual visually analyzes the medical image 302 to identify at least one point on the patient's body (e.g., spine 314) shown in the medical image 302. In the spine scenarios, each point can include, but is not limited to, a point on a femur, a cervical vertebra C1-C8, a thoracic vertebra T1-T12, a lumbar vertebra L1-L5, a sacral vertebra S1-S4 or other part along the vertebral column of the patient (e.g., patient 104 of FIG. 1). An illustration showing the listed types of vertebrae is provided in FIG. 4.

Once the point(s) on the patient's body (e.g., spine 314) has(have) been identified, a mark is overlaid or superimposed on the medical image 302 for each identified point. Techniques for overlaying or superimposing marks on images are well known. Any known or to be known technique can be used herein. For example, a mark can be overlaid or superimposed on the medical image 302 via user-software interactions performed by the individual using an annotation or drawing tool of the software application. The present solution is not limited in this regard. Annotation and drawing tools are well known.

The mark can include, but is not limited to, a line, a circle, and/or a square. For example, a circular mark 315 is drawn on the medical image 302 so as to encompass a femoral edge. A first linear mark 316 is drawn on the medical image 302 so as to extend parallel to and/or along an top end plate of a sacral vertebrae S1. A second linear mark 317 is drawn on the medical image 302 so as to extend parallel to and/or along a top end plate of a lumbar vertebrae L1. The present solution is not limited to the particulars of this example.

Next in 308, the computing device performs operations to generate, create or select a spline based on the machine learned models and/or the marks 315, 316, 317 overlaid/superimposed on the medical image 302. In some scenarios, the computing device inputs information about the marks 315, 316, 317 into a machine-learning algorithm. The machine-learning algorithm can employ supervised machine learning, semi-supervised machine learning, unsupervised machine learning, and/or reinforcement machine learning. Each of these listed types of machine-learning is well known in the art.

In some scenarios, the machine-learning algorithm includes, but is not limited to, a decision tree learning algorithm, an association rule learning algorithm, an artificial neural network learning algorithm, a deep learning algorithm, an inductive logic programming based algorithm, a support vector machine based algorithm, a Bayesian network based algorithm, a representation learning algorithm, a similarity and metric learning algorithm, a sparse dictionary learning algorithm, a genetic algorithm, a rule-based machine-learning algorithm, and/or a learning classifier systems based algorithm. The machine-learning process implemented by the present solution can be built using Commercial-Off-The-Shelf (COTS) tools (e.g., SAS available from SAS Institute Inc. of Cary, N.C.).

The machine-learning algorithm uses the inputted information and the previously generated machine learned models to generate/create a spline using curve fitting and/or select a pre-defined spline from a plurality of pre-defined possible splines. Curve fitting is well known in the art. In some scenarios, the spline includes a piecewise polynomial curve. Accordingly, a mathematical function may be employed to generate the spline as an alternative to or in addition to the machine-learning algorithm. The mathematical function can be defined by one or more polynomial equations representing one or more numerically complex contours on a given body part (e.g., a spine).

A mark for the spline is then overlaid or superimposed on the medical image 302. For example, a curved line 318 is overlaid or superimposed on the medical image 302 as shown in FIG. 3. Line 318 extends between the first mark 316 and the second mark 317. Line 318 starts at a mid-point 324 of the first mark 316 and ends at a mid-point 326 of the second mark 317. In effect, the line 318 generally follows and extends along a centerline of the vertebrae L1-L5. The present solution is not limited in this regard.

The mark 318 may be presented to the individual via the display (e.g., display 254 of FIG. 2) of the computing device. In some scenarios, the software application is configured to (i) allow the individual to adjust or modify the mark 318 and/or (ii) approve the mark 318, prior to proceeding with the operations of 310.

Figure 5:
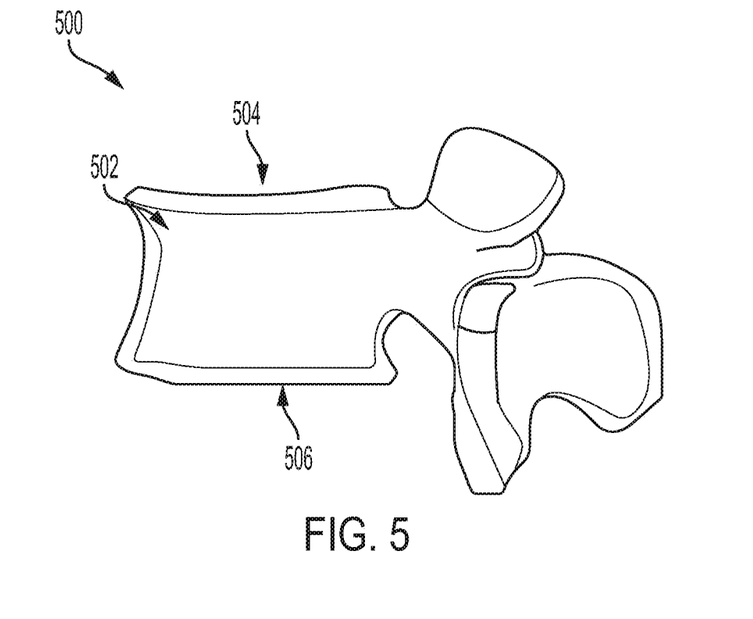
FIG. 5 provides an illustration of a vertebra.

In 310, the computing device performs operations to identify locations and/or positions of vertebra endplates in the medical image 302. As shown in FIG. 5, a vertebral endplate 504, 506 of a vertebrae 500 comprises a surface defining a transition region where a vertebral body 502 and an intervertebral disc (not shown) interface with each other. These identifications can be made based on the machine learned models, the marks 315, 316, 317, 318 overlaid/superimposed on the medical image 302, and/or contents of scientific database (e.g., datastore 116 of FIG. 1 that stores models of a normal spine and relative vertebrae locations/positions). In some scenarios, the computing device inputs information about the marks 315, 316, 317, 318 into a machine-learning algorithm. The machine-learning algorithm can be the same as or different than the machine-learning algorithm employed in 308.

The machine-learning algorithm uses inputted information about marks 315, 316, 317, 318 and the previously generated machine learned models to generate or select possible locations/positions for vertebrae endplates. For example, the machine-learning algorithm can determine a location or position of a vertebrae endplate based on a body part identifier (e.g. L1 or S1) associated with each mark 315, 316, 317, a distance between marks 316, 317 in the medical image 302, a distance between mark 315 and each mark 316, 317 in the medical image 302, a location of spline mark 318 in the medical image 302, a shape of the spline mark 318, a curvature of the spline mark 318, an angle 330 of mark 316 relative to a reference line 328, and an angle 332 of mark 317 relative to the reference line 328. The listed information is used to identify a machine learned model from a plurality of pre-defined machine learned models. The locations/positions for vertebrae endplates specified in the identified machine learned model are then considered to be the locations/positions of vertebrae endplates in the medical image 302. The present solution is not limited to the particulars of this example.

A mark 320 is overlaid or superimposed on the medical image 302 at each identified location or position for a vertebra endplate. Each mark 320 can include, but is not limited to, a linear line. The mark 320 can have a center point 340 that resides on the spline mark 318 such that the linear line extends an equal amount in opposing directions from the spline mark 318.

The mark(s) 320 may be presented to the individual via the display (e.g., display 254 of FIG. 2) of the computing device. In some scenarios, the software application is configured to (i) allow the individual to adjust or modify the mark(s) 320 and/or (ii) approve the mark(s) 320, prior to proceeding with the operations of 312.

In 312, the computing device performs operations to address any errors in the positions/locations/sizes of the mark(s) 320 in the medical image 302. These operations involve defining circles 334 within the medical image 302. Each circle 334 has a pre-defined size and encompasses an end point 336 of a given mark 320. The computing device then analyzes the area of the medical image contained in each circle 334 to determine a precise location of a vertebrae's corner. For example, the computing device analyzes differences in pixel color, gray level and/or contrast within the given area to determine the precise location of a vertebrae's corner. As shown in FIG. 3, the pixel(s) associated with the vertebrae's corner has(have) a weaker gray level than the pixels associated with a surrounding structure. This difference in color, gray level and/or contrast is used to identify the precise location of a vertebrae's corner. The present solution is not limited to the particulars of this example.

Once the precise location(s) of the vertebrae corner(s) is(are) identified, the computing device may perform operations to adjust or modify the shape(s), size(s) and/or location(s) of the mark(s) 320 relative to the medical image 302. For example, a length of a given mark 320 is increased or decreased, and/or an angle of a given mark 320 is changed relative to the reference line 328 based on displacements or differences between the locations of the mark corners and the respective precise locations(s) of vertebrae corner(s). The present solution is not limited to the particulars of this example.

Subsequent to completing the operations of 312, the computing device may use information about the marks 315, 316, 317, 318 and/or 320 to create a treatment plan for the patient. For example, the information about the marks 315, 316, 317, 318 and/or 320 is used by the computing system to identify a possible abnormal condition or medical disease of the patient and/or make a prediction about a future medical disease or abnormal condition for the patient. This identification/predication can be made by comparing the particulars of marks 315, 316, 317, 318 and/or 320 to particulars of marks contained in pre-defined machine learned module(s). An abnormal condition or medical disease is identified/predicted when the particulars of the marks 315, 316, 317, 318 and/or 320 match the particulars of marks contained in pre-defined machine learned module(s) by a certain amount (e.g., 70%). The identified or predicted medical disease or abnormal condition is then used to generate a treatment plan. The treatment plan comprises an electronic and/or paper document that describes the patient's individualized diagnosis, needs, goals, treatment interventions and treatment providers. The treatment plan may also include measurements of radiographic parameters (e.g., spinopelvic and frontal) at different stages (e.g., preoperatively and surgical planning stages). The radiographic measurements can include, but are not limited to, pelvic tilt, pelvic incidence, sacral slope, lumbar lordosis, thoracic kyphosis, pelvic angle, sagittal vertical axis, and vertebra lordosis. The treatment plan may further include planning specifications (e.g., a rod is to be lengthened according to coronal deformity).

In some scenarios, a treatment system (e.g., treatment system 150 of FIG. 1) may then be programmed such that it can perform operations in accordance with the treatment plan. The treatment system can include, but is not limited to, an implant creating system, a surgical tool, and/or a radiation therapy device. Each of the listed treatment systems are well known. The treatment system may then perform operations to (i) produce, locate, order or otherwise obtain a medical device to be implanted in the patient (e.g., a cage, a hook, a plate, a screw, a rod and/or a spinal cord stimulator) and/or (ii) apply a treatment to the patient during a medical procedure (e.g., facilitate the control of and/or the implanting of one or more medical devices or tools).

The above described solution can be employed and incorporated in other systems such as those disclosed in U.S. patent application Ser. No. 16/837,461, U.S. patent application Ser. No. 16/404,276, U.S. patent application Ser. No. 15/958,409, U.S. patent application Ser. No. 16/182,466, and International Patent Application No. PCT/FR17/053506. The entire contents of which are incorporated herein by reference.

Figure 6A:
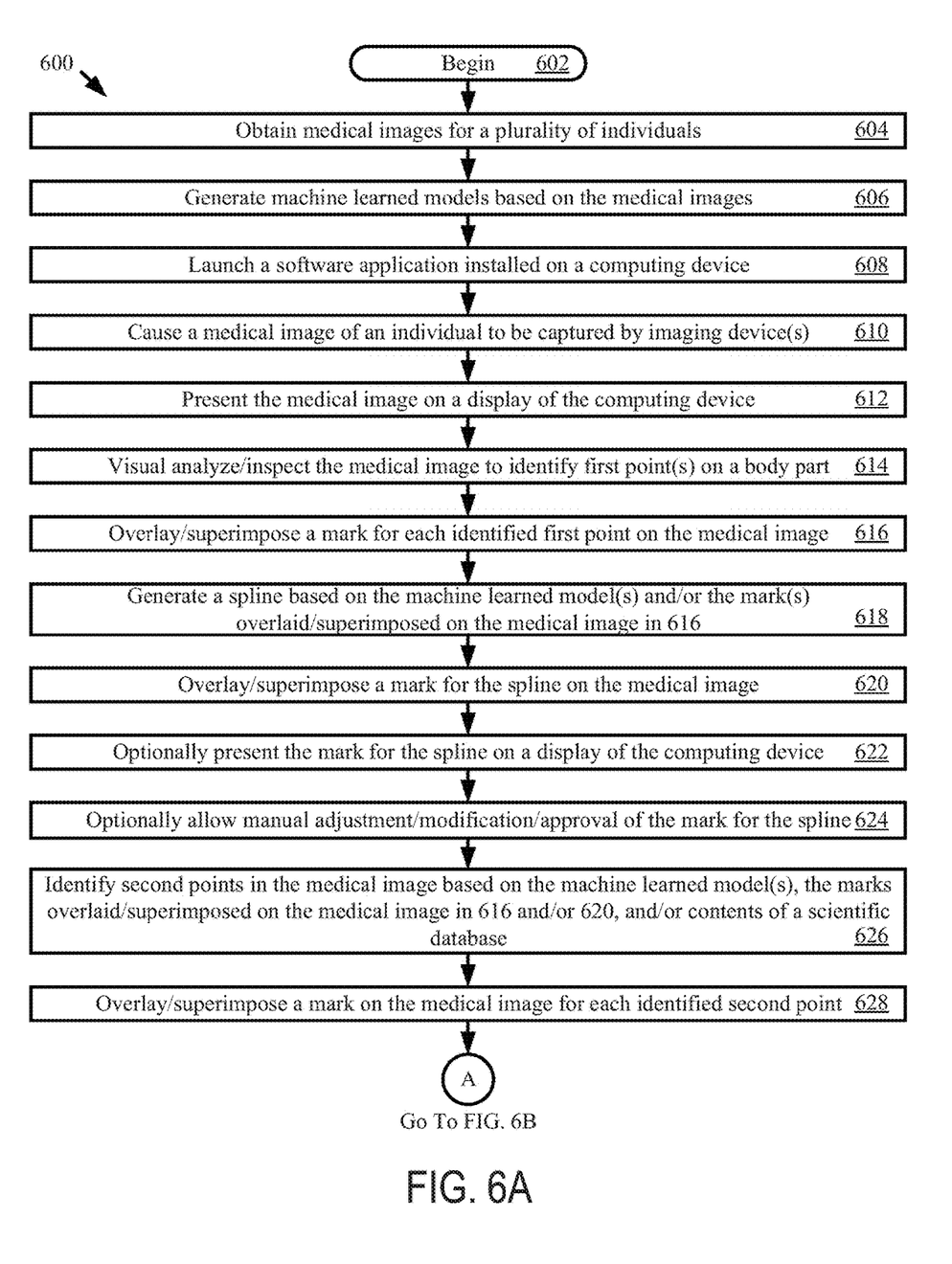
FIGS. 6A-6B (collectively referred to as "FIG. 6") provide a flow diagram of an illustrative method for medical treatment.

Referring now to FIG. 6, there is provided a flow diagram of an illustrative method 600 for medical treatment. As shown in FIG. 6A, method 600 begins with 602 and continues with 604 where medical images for a plurality of individuals are obtained. The medical images can include, but are not limited to, a DT scan image, a CT scan image, an MRI image, and/or a PET scan image. In 606, machine learned models are generated based on the medical images. Each machine learned model represents a possible structure of a body part (e.g., a spine). For example, each machine learned model may define relative locations of a femoral edge to vertebrae, relative locations of vertebrae to each other, dimensions of vertebrae, relative locations of vertebrae edges, angles of vertebrae edges relative to a reference line, a centerline of the spine, and a curvature of the centerline. The present solution is not limited to the particulars of this example.

In 608, a software application (e.g., software application 224 of FIG. 2) is launched. Techniques for launching software applications installed on computing devices are well known in the art. The software application is configured to cause a medical image (e.g., medical image 302 of FIG. 2) of an individual (e.g., individual 104 of FIG. 1) to be captured by at least one imaging device (e.g., imaging device(s) 102 of FIG. 1). The medical image is presented on a display (e.g., display 254 of FIG. 2) of a computing device (e.g., computing device 108 of FIG. 1, server 114 of FIG. 1, and/or computing device 200 of FIG. 2).

Next in 614, the medical image is visually analyzed or inspected to identify point(s) on a body part shown therein. For example, one or more vertebrae endplates of a spine is identified in the medical image. A mark is overlaid or superimposed on the medical image for each identified point, as shown by 616. An annotation tool or drawing tool can be used to overlay or superimpose the mark(s) on the medical image.

In 618, a spline is generated based on the machine learned model(s) and/or particulars of the mark(s) overlaid/superimposed on the medical image in 616. The spline may be generated in the same or substantially similar manner as that described above in relation to FIG. 3. A mark for the spline is overlaid/superimposed on the medical image in 620. The mark for the spine may be presented on the display of the computing device, as shown by 622. Manual adjustments to, modifications to and/or approval of the spline mark may optionally be allowed in 624. The manual actions can be achieved using one or more widgets of a Graphical User Interface (GUI) presented on the display of the computing device. The GUI can be the same as or different than the GUI in which the medical image is displayed.

In 626, the computing device performs operations to identify second point(s) on the body part shown in the medical image. For example, the computing device identifies location(s) and/or position(s) of vertebra endpoint(s) in a spine shown in the medical image. The manner in which the identification(s) is(are) made is the same as or substantially similar to that described above in relation to FIG. 3. In this regard, the identification(s) is(are) made based on the machine learned model(s), the marks overlaid/superimposed on the medical image in 616 and/or 620, and/or contents of a scientific database (e.g., database 116 of FIG. 1).

In 628, a mark is overlaid or superimposed on the medical image for each identified second point (e.g., location/position for a vertebrae endplate). Upon completing 628, method 600 continues with 630 of FIG. 6B.

Figure 6B:
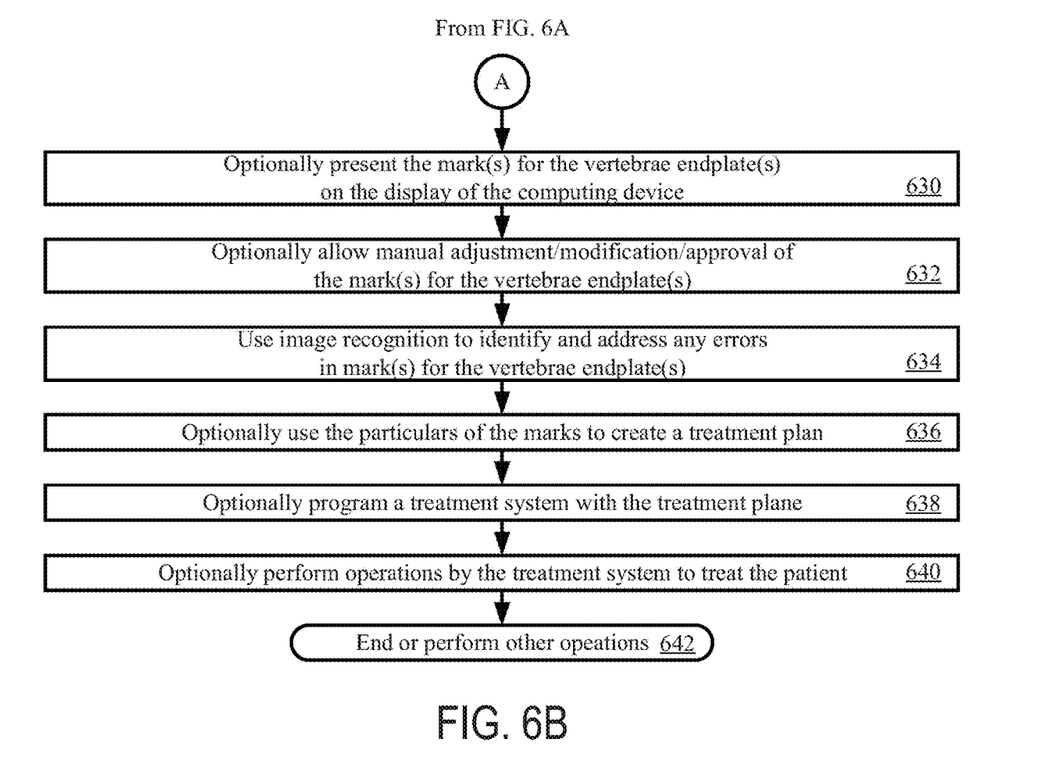

As shown in FIG. 6B, 630 involves optionally presenting the mark(s) for the vertebrae endplates on the display of the computing device. The software application may allow manual adjustments to, modification of and/or approval of the mark(s) for the vertebra endplates, as shown by 632. The manual actions can be achieved using one or more widgets of a GUI presented on the display of the computing device. The GUI can be the same as or different than the GUI in which the medical image is displayed.

In 634, image recognition is used to identify and address any errors in mark(s) for the vertebrae endplate(s). The manner in which the image recognition is performed is the same as or substantially similar to that described above in relation to block 312 of FIG. 3. Next, method 600 may continue with 636, 638 and/or 640. 636-640 involve: using the particulars of the marks to create a treatment plane; programming a treatment system (e.g., treatment system 150 of FIG. 1) with the treatment plan; and/or performing operations by the treatment system to treat the individual. Subsequent to completing 634, 636, 638 or 640, 642 is performed where method 600 ends other operations are performed (e.g., return to 602 of FIG. 6A).

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A method for medical treatment, comprising:
receiving, by a computing device, information identifying at least one first point on a body part shown in a medical image;
overlaying, by the computing device, a first mark on the medical image for the at least one first point;
generating, by the computing device, a spline based at least on the first mark;
overlaying, by the computing device, a second mark for the spline on the medical image;
identifying, by the computing device, a location of at least one second point on the body part shown in the medical image based on the first and second marks;

overlaying, by the computing device, a third mark for the at least one second point on the medical image;

analyzing differences in gray levels for pixels residing within a given area surrounding an end of the third mark to determine a precise location of an object corner; and modifying at least one of a shape of the third mark, a size of the third mark and a location of the third mark relative to the medical image in accordance with results of the analyzing; and using at least the third mark to facilitate the medical treatment of an individual whose body part is shown in the medical image.

2. The method according to claim 1, further comprising performing operations, by the computing device, to cause an imaging device to capture the medical image.

3. The method according to claim 1, wherein at least one machine learned model is additionally used to generate the spline.

4. The method according to claim 3, wherein the at least one machine learned model defines a possible structure of a spine.

5. The method according to claim 1, wherein the spline comprises a piecewise polynomial curve.

6. The method according to claim 1, wherein the second mark comprises a curved line that (i) extends between a mid-point of the first mark and a mid-point of another mark, and (ii) extends along a centerline of the body part.

7. The method according to claim 1, wherein the first and second points comprise vertebrae endpoints.

8. The method according to claim 1, wherein the location of the at least one second point is identified further based on at least one of a machine learned model and contents of a scientific database.

9. The method according to claim 1, wherein the precise location of the object corner is determined by:

defining a circle within the medical image that encompasses an end point of the third mark; and considering the given area as comprising an area of the medical image contained in the circle.

10. A system, comprising:

a processor;

a non-transitory computer-readable storage medium comprising programming instructions that are configured to cause the processor to implement a method for medical treatment, wherein the programming instructions comprise instructions to:

receive information identifying at least one first point on a body part shown in a medical image;

overlay a first mark on the medical image for the at least one first point;

generate a spline based at least on the first mark;

overlay a second mark for the spline on the medical image;

identify a location of at least one second point on the body part shown in the medical image based on the first and second marks;

overlay a third mark for the at least one second point on the medical image;

analyze differences in gray levels for pixels residing within a given area surrounding an end of the third mark to determine a precise location of an object corner; and modify at least one of a shape of the third mark, a size of the third mark and a location of the third mark relative to the medical image in accordance with results of the analyzing; and use at least the third mark to facilitate the medical treatment of an individual whose body part is shown in the medical image.

11. The system according to claim 10, wherein the programming instructions further comprise instructions to cause an imaging device to capture the medical image.

12. The system according to claim 10, wherein at least one machine learned model is additionally used to generate the spline.

13. The system according to claim 12, wherein the at least one machine learned model defines a possible structure of a spine.

14. The system according to claim 10, wherein the spline comprises a piecewise polynomial curve.

15. The system according to claim 10, wherein the second mark comprises a curved line that (i) extends between a mid-point of the first mark and a mid-point of another mark, and (ii) extends along a centerline of the body part.

16. The system according to claim 10, wherein the first and second points comprise vertebrae endpoints.

17. The system according to claim 10, wherein the location of the at least one second point is identified further based on at least one of a machine learned model and contents of a scientific database.

18. The system according to claim 10, wherein the precise location of an object corner is determined by:

defining a circle within the medical image that encompasses an end point of the third mark; and considering the given area as comprising an area of the medical image contained in the circle.

* * * * *